United States Patent [19]

Brown et al.

[11] 4,290,966

[45] Sep. 22, 1981

[54] PROCESS FOR THE PREPARATION OF TRAUMATIN

[75] Inventors: Jeannette E. Brown, Summit; Edward F. Rogers, Middletown; Donald W. Graham, Mountainside, all of N.J.

[73] Assignee: Merck & Co., Inc., Rahway, N.J.

[21] Appl. No.: 193,790

[22] Filed: Oct. 3, 1980

[51] Int. Cl.$^3$ .............................................. C11C 1/00
[52] U.S. Cl. ..................................... 260/413; 260/406
[58] Field of Search ................ 260/406, 413 R, 413 Q

[56] References Cited

PUBLICATIONS

Kajiwara et al., Agric. Biol. Chem., 41 (9) pp. 1793–1794 (1977).
Bestmann et al., Tet. Lett., 1, pp. 121–124 (1977).
Yamamoto et al., Chem. Lett., pp. 859–862 (1978).
Rakoff et al., Synthetic Comm., 9, pp. 185–199 (1979).

*Primary Examiner*—John F. Niebling
*Attorney, Agent, or Firm*—Frank M. Mahon; Hesna J. Pfeiffer

[57] ABSTRACT

Traumatin, 12-oxo-trans (E) -10-docecenoic acid, is prepared from 10-oxomethyldecanoate by reaction with (triphenylphosphoranylene)acetaldehyde to form 12-oxomethyldodecenoate; blocking the 12-oxo group; hydrolyzing the ester group; and deblocking the 12-oxo group.

6 Claims, No Drawings

PROCESS FOR THE PREPARATION OF TRAUMATIN

This invention relates to a process of the chemical synthesis of traumatin, a known plant wound hormone and bioregulant.

Traumatin is an oxidation product of polyunsaturated fatty acids in plant tissues. This compound has now been identified as 12-oxo-trans (E)-dodecenoic acid having the structure:

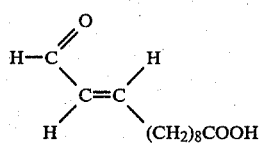

Traumatin is recognized as displaying wound hormone activity and growth stimulation in a variety of plant tissues. It is, therefore, a potent bioregulant.

Heretofore, traumatin has been obtained by isolation from natural plant products, while synthesis of this compound has reported by destructive oxidation of a natural plant product, it is probable that the product actually obtained was the cis (Z) isomer. In addition, various syntheses of the ester of traumatin are reported in the literature but no synthesis of the trans (E) acid is reported.

The instant invention, therefore, is based upon applicant's discovery of a process for the chemical synthesis of traumatin. More particularly, the instant invention resides in applicants' concept of a process for the chemical synthesis of traumatin which is stereospecific for the trans (E) isomer and in which the acid is obtained directly, not the ester.

The following diagram illustrates the synthesis of traumatin according to the instant invention.

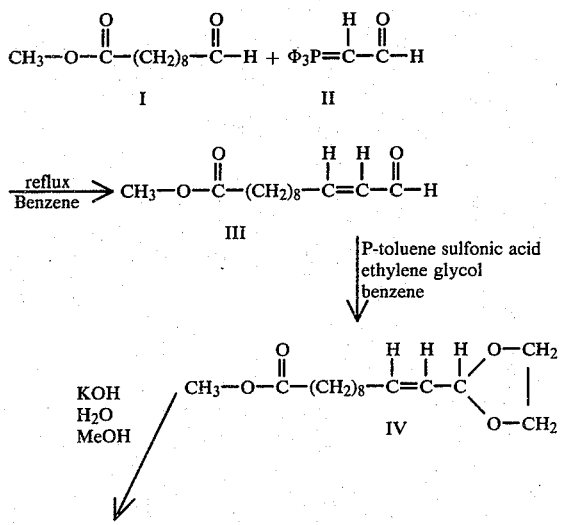

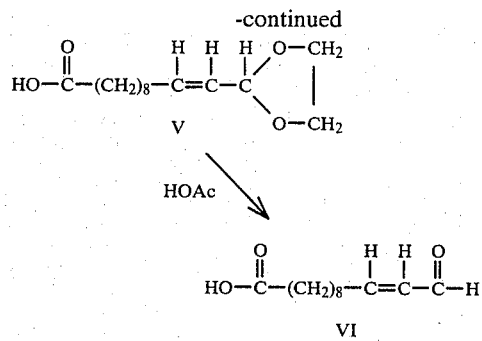

As may be seen from the foregoing diagram, traumatin is prepared according to the process of the instant invention by treating 10-oxomethyldecanoate (I) with (triphenylphosphoranylene)acetaldehyde (II) to obtain 12-oxomethyldodecenoate (III). The reaction is carried out in the presence of a non-polar organic solvent such as benzene, hexane, toluene or the like. Desirably the reaction is run at reflux and usually is complete in 8–16 hours. The oxododecenyl ester so produced then is refluxed with ethylene glycol, desirably in the presence of a non-polar organic solvent such as mentioned above and a catalytic quantity of para-toluene sulfonic acid, to obtain the acetal (IV), methyl 11-(1,3-dioxalane-2-yl)-10-undecenoate. This reaction usually requires 12–24 hours for completion. Hydrolysis of this ester with an aqueous alcoholic alkali metal or alkanine earth metal hydroxide gives the corresponding acid (V). The reaction is run at reflux and usually is complete in 30–90 minutes. Finally, the acid (V) is refluxed with a suitable organic acid such as acetic acid for 1–4 hours to obtain the desired traumatin (VI).

The best mode contemplated by applicants for carrying out the instant invention is illustrated in the following working example; no limitation being intended except as set forth in the appended claims.

EXAMPLE I

12-Oxo-trans (E)-10-dodecenoic Acid

Step A: 12-Oxomethyldodecenoate

Mix with stirring 2.0 g (0.01 mole) of 10-oxomethyldecanoate, 32 g. of (triphenylphosphoranylene)-acetaldehyde and 150 ml of benzene. Reflux overnight, cool to room temperature and concentrate to dryness. Take up the residue in petroleum ether, filter and wash with petroleum ether. Concentrate the filtrate to dryness. Take up the residue in petroleum ether and chromatograph on 80 g of silica-gel. Elute with ether/petroleum ether (25/75) to obtain 1.6 g of the title product.

Step B: Methyl 11-(1,3-Dioxalane-2-yl)-10-Undecenoate

Mix with stirring the product of Step A, 0.55 ml of ethylene glycol, 5 ml of benzene and 5 mg of p-toluene sulfonic acid. Reflux for 22 hours. Pour the reaction mixture into water and extract with saturated aqueous sodium bicarbonate solution then water (brine). Dry over sodium sulfate, filter and concentrate to dryness to obtain the title product (1.7 g).

Step C: 11-(1,3-Dioxalane-2-yl)-10-Undecenoic Acid

Mix with stirring the product of Step B, 0.55 g of potassium hydroxide, 2.5 ml of water and 2.5 ml of methanol. Reflux for 1 hour and pour the reaction mixture into water. Acidify with concentrated hydrochloric Acid. Extract with ether and wash the ether solution with water. Dry the ether solution over sodium sulfate, filter and concentrate to dryness to obtain the title product. Step D: 12-Oxo-trans (E)-10-decenoic Acid Add 10 ml of 50% aqueous acetic acid to the product of Step C. Stir and reflux for 2 hours. Pour the reaction mixture into brine. Extract with ether. Extract the ether solution 3 times with water. Dry the ether solution over sodium sulfate, filter and concentrate to dryness to obtain the title product (400+ mg).

Analysis: $C_{12}H_2O_3$: M.W. 212.3: Calc.: C67.89; H 9.50. Fd.: C66.68; H 9.53.

The subject matter which applicants regard as their invention is particularly pointed out and distinctly claimed as follows:

1. A process for the preparation of traumatin which comprises:
    (a) treating 10-oxomethyldecanoate in a non-polar organic solvent with (triphenylphosphoranylene)acetaldehyde to obtain 12-oxomethyldodecenoate;
    (b) treating the product of Step (a) with ethylene glycol in a non-polar organic solvent to obtain methyl 11-(1,3-dioxalane-2-yl)-10-undecenoate;
    (c) hydrolyzing the product of Step (b) to obtain 11-(1,3-dioxalane-2-yl)-10-undecenoic acid; and
    (d) hydrolyzing the product of Step (c) to obtain traumatin.

2. The process of claim 1 wherein the non-polar organic solvent is benzene.

3. The process of claim 2 wherein the reaction with ethylene glycol is carried out in the presence of a catalytic quantity of p-toluene sulfonic acid.

4. The process of claim 3 wherein the hydrolysis of Step (c) is carried out with an aqueous alcoholic alkali metal hydroxide.

5. The process of claim 4 wherein the alkali metal hydroxide is potassium hydroxide.

6. The process of claim 5 wherein the hydrolysis is carried out with acetic acid.

* * * * *